United States Patent
Bocionek

(10) Patent No.: US 7,149,779 B2
(45) Date of Patent: Dec. 12, 2006

(54) MEDICAL SYSTEM ARCHITECTURE WITH MODALITIES FOR ACQUIRING EXAMINATION IMAGES, LINKED WITH A COMMUNICATION SYSTEM

(75) Inventor: Siegfried Bocionek, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 565 days.

(21) Appl. No.: 09/999,729

(22) Filed: Oct. 24, 2001

(65) Prior Publication Data

US 2002/0091765 A1   Jul. 11, 2002

(30) Foreign Application Priority Data

Oct. 24, 2000   (DE) ................... 100 52 817
Oct. 8, 2001    (DE) ................... 101 49 482

(51) Int. Cl.
*G06F 15/16* (2006.01)

(52) U.S. Cl. .................. 709/206; 709/218; 378/62

(58) Field of Classification Search ............ 709/206, 709/207, 217; 600/425, 437; 378/62
See application file for complete search history.

(56) References Cited

U.S. PATENT DOCUMENTS 6,260,021 B1 *  7/2001  Wong et al. ............... 705/2
6,424,996 B1 *  7/2002  Killcommons et al. ..... 709/206
6,574,629 B1 *  6/2003  Cooke et al. ............... 707/10
6,574,742 B1 *  6/2003  Jamroga et al. ........... 713/400
6,789,107 B1 *  9/2004  Bates et al. ................ 709/206

FOREIGN PATENT DOCUMENTS

| DE | OS 196 25 839 | 1/1998 |
| DE | 200 03 469 | 9/2000 |

* cited by examiner

*Primary Examiner*—David Wiley
*Assistant Examiner*—Phuoc H. Nguyen
(74) *Attorney, Agent, or Firm*—Schiff Hardin LLP

(57) ABSTRACT

A medical system architecture has a modality for acquiring examination images, a device allocated to the modality for processing the examination images, a device for transmission of data and the examination images, a device for storing the data and examination images, and further devices for post-processing the data and examination images, and a message system, such as an e-mail server, for receiving and sending messages by e-mail is allocated to the devices for processing and post-processing the examination images.

15 Claims, 2 Drawing Sheets

MEDICAL SYSTEM ARCHITECTURE WITH MODALITIES FOR ACQUIRING EXAMINATION IMAGES, LINKED WITH A COMMUNICATION SYSTEM

BACKGROUND OF THE INVENTION

1. Field of the Invention

The present invention is directed to a medical system architecture of the type having a modality for acquiring examination images, a device allocated to the respective modality for processing the examination images, a device for the transmission of data and the examination images, a device for storing the data and examination images, and further devices for post-processing the data and examination images.

2. Description of the Prior Art

System architectures of this type serve, for example in hospitals, for generating and processing medical examination images or to prepare diagnoses of patients.

The book "Bildgebende Systeme für die medizinische Diagnostik," edited by H. Morneburg, $3^{rd}$ Edition, 1995, pages 684 ff. discloses medical system architectures, referred to as PACS (Picture Archival and Communication Systems) wherein image viewing and image processing locations, referred to as work stations, are connected to one another via an image communication network for fetching patient data and images generated by modalities.

German Utility 200 03 469 discloses a hand-held computer for the display and processing of medical data. Such a hand-held computer makes it possible to carry the electronic patient files as well as a number of additionally interesting medical data such as, for example, image data along in mobile fashion, for example when the physician visits the hospital bed. The data exchange with existing computer systems ensues with interfaces. The data also can be transmitted by e-mail.

In a medical modality, the emergency admitting staff of a hospital can designate an accident victim with whom a fast overview diagnosis is to be immediately carried out by telephone, which can greatly disrupt normal operations. Such a designation also can ensue via additional computers in the proximity of the modality, but it is not assured that this emergency report will also be immediately noticed.

The client software of a radiology information system (RIS) is the user interface for medical-technical radiology assistants (MTRA) and physicians in radiology in order, for example, to admit patients, plan examinations and terminate them, to administer the findings and initiate billings. Dependent on how this is embedded in the higher-ranking hospital information system (KIS), some of the events can already ensue via the interface such as, for example, the patient admitting, performance requests and billing, and the RIS merely accepts the data coupled with these events via a network interface.

In addition to these "administrative activities", the RIS often also acts as workflow driver in radiology in order, for example, to send request data in the form of a DICOM worklist entry to a modality such as a CT, MR or X-ray device at which the examination is to take place. Given current systems, the examination data, for example, a number of images, series and radiation protection data such as tube voltage (kV), mAs product (mAs), time (s), energy dose (Gy), etc., must be manually read by a worker and transmitted into the RIS for the required transfer of the examination data from the modality into the RIS for documentation and billing, a considerable outlay and additional sources of error occurs as a result.

SUMMARY OF THE INVENTION

An object of the invention is to design the devices for processing and post-processing of the examination images for improving the workflow by dependable and fast acceptance of emergency messages.

This object is inventively achieved in a medical system architecture of the type initially described having a message system linked into the medical workflow and allocated to the devices for processing and post-processing of the examination images, the message system being connected to a server as client of an information system. The server can be an RIS server, a workflow server or an e-mail server. The user of a medical modality can receive and send digital messages by e-mail at his or her console workstation electronically, so that the workflow in the radiology is significantly improved, for example due to the linking of the MTRAs working at the modalities. Such medical modalities can, for example, be an MR, CT, ultrasound, X-ray or angiography device, nuclear camera, supervision monitor, diagnostic workstation or irradiation device.

The devices can have monitors, fashioned such that e-mail applications, e-mail services and/or e-mail messages can be mixed in a window on the respective monitors in addition to the examination images.

Emergency messages are noticed especially well when the devices are fashioned such that, when e-mails are sent, an e-mailed marked dependent on the importance and, when e-mails marked as important are received, these are mixed in a window on the monitor with priority, whereas an indicator is merely generated given less important e-mails. The devices can have an acoustic or optical signal generator that emits an acoustic or optical signal upon receipt of marked e-mails.

Adequate security is assured when the devices effect an encryption of the data.

The devices can be a level 7 application according to the ISO-OSI layer model for communication protocols.

DESCRIPTION OF THE PREFERRED EMBODIMENTS

Figure 1:
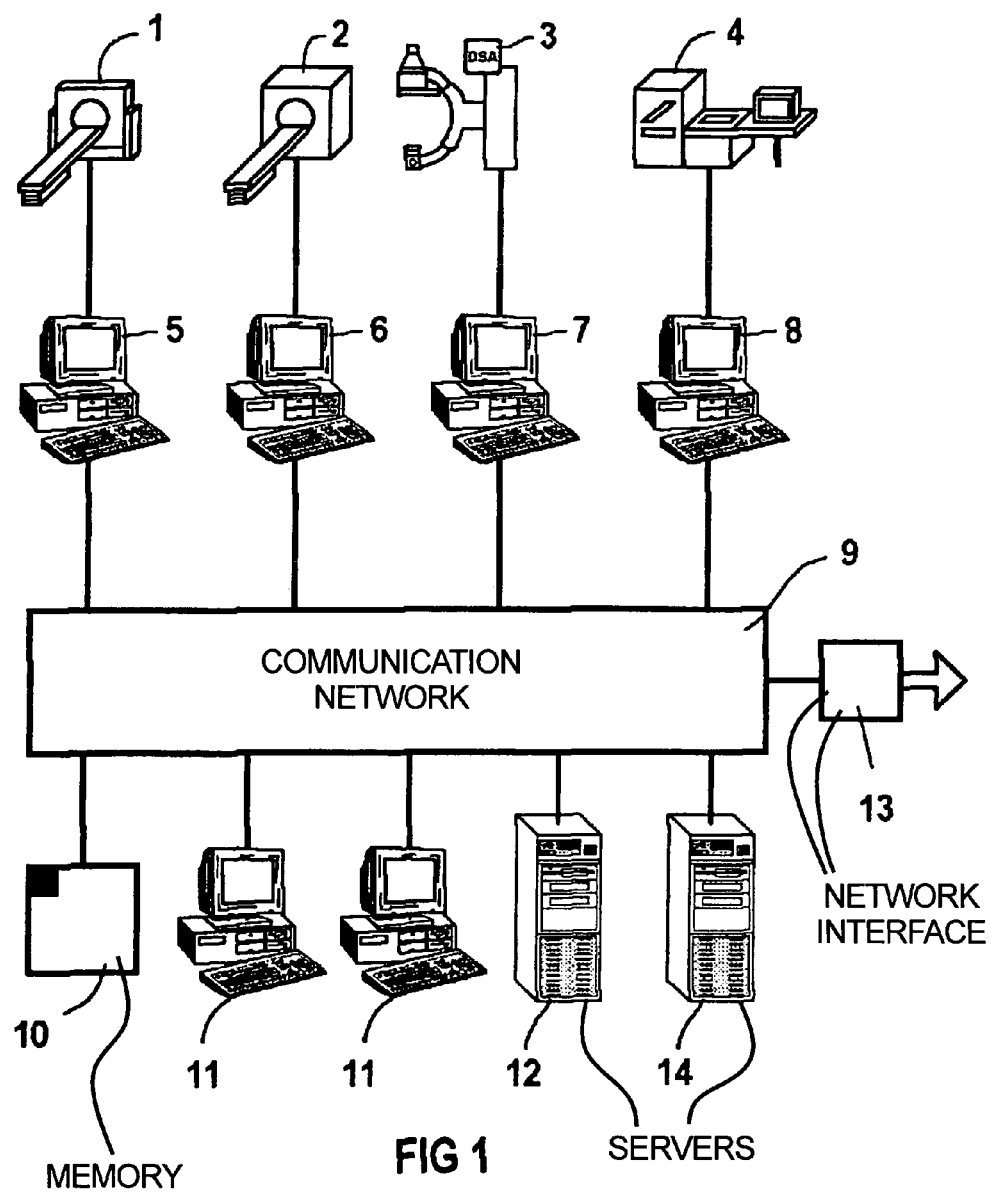
FIG. 1 is a schematic illustration of an embodiment of a system architecture of a hospital network.

FIG. 1 shows the system architecture of a hospital network as an example. The modalities 1 through 4 serve for the acquisition of medical images; such as a CT unit 1 for computed tomography, an MR unit 2 for magnetic resonance, a DSA unit 3 for digital subtraction angiography and an X-ray unit 4 for digital radiography 4, as image-generating systems. Operator consoles 5 through 8 of the modalities or workstations are connected to these modalities, the acquired medical images are able to be processed and locally stored therewith. Patient data belonging to the images also can be entered.

For linking to a PACS, the operator consoles 5 through 8 are connected to a communication network 9 as LAN/WAN backbone for distributing the generated images and for communication. Thus, for example, the images generated in the modalities 1 through 4 and the images that are further-processed in the operator consoles 5 through 8 can be stored in central image storage and image archiving systems 10 or can be forwarded to other workstations.

Further viewing workstations 11 are connected to the communication network 9 as diagnostic consoles that have local memories. For example, such a viewing workstation 11 is a very fast mini computer on the basis of one or more fast processors. The images that are acquired and stored in the image archiving system can be subsequently called in the viewing workstations 11 for diagnosis and can be stored in a local image memory, from which they can be immediately available to the diagnostician working at the viewing workstation 11.

Further, servers 12, for example patient data servers (PDS), file servers, program servers and/or EPR servers, are connected to the communication network 9.

The image and data exchange via the communication network 9 ensues according to the DICOM standard, an industry standard for the transmission of images and further medical information between computers, so that digital communication between diagnosis and therapy devices of different manufacturers is possible. A network interface 13 via which the internal communication network 9 is connected to a global data network, for example the world wide web, can be connected to the communication network 9, so that the standardized data can be exchanged with different networks world-wide.

An RIS server 14 is connected to the communication network 9, this coordinating the sending and receiving of e-mails within the communication network 9 and from outside via the network interface 13 as well.

Figure 2:
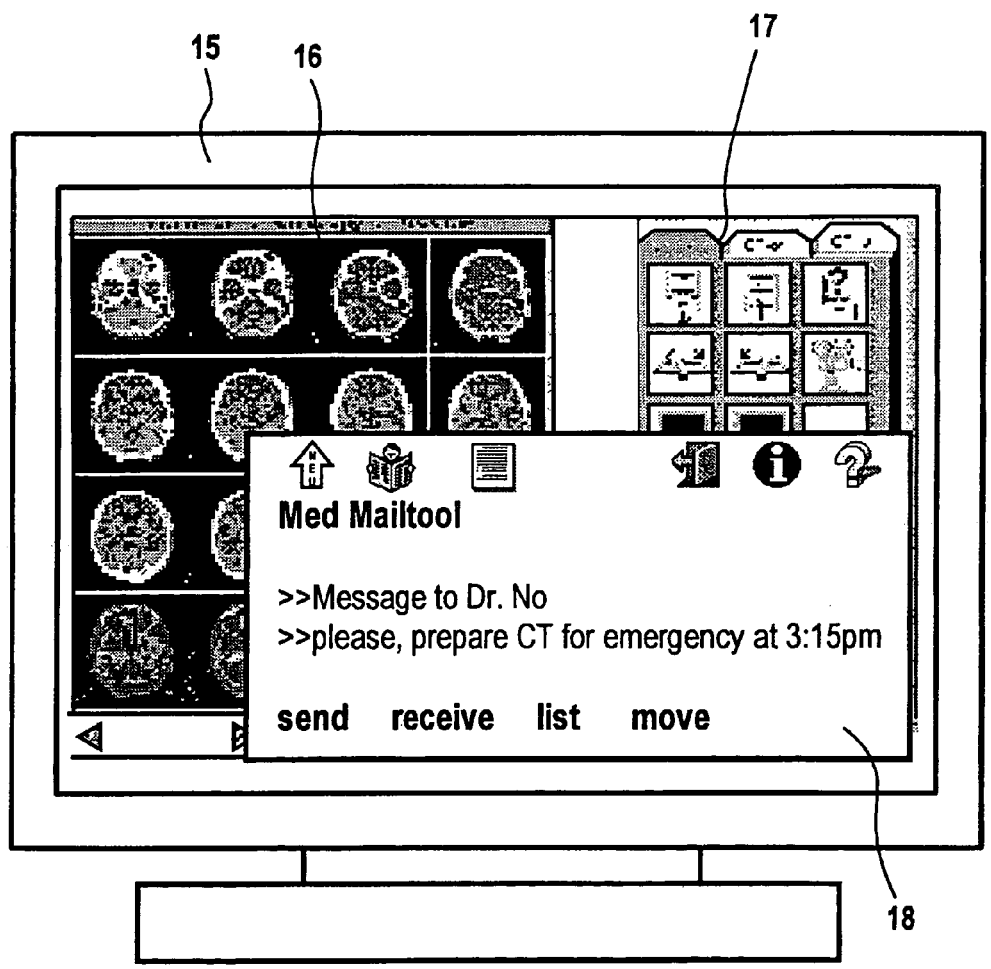
FIG. 2 is a schematic illustration of a monitor of the inventive system architecture.

FIG. 2 shows a monitor 15 of a console or backup console computer, for example the operator console 5 of the CT unit 1. An image processing window 16 with a number of juxtaposed CT exposures is shown on the monitor 15, a control area 17 with icons for launching commands being arranged next to the window 16 in a known way.

When an e-mail message is received at the CT operator console 5, which signifies, for example, that a whole-body CT scan of an accident victim for a fast overview diagnosis should immediately ensue, then an e-mail window 18 is opened on the monitor 15 controlled by the RIS server 14. Given an emergency admission in the hospital, this e-mail window 18 is placed overall user windows 16 and 17, so that it can be immediately noticed in order for the workflow to be correspondingly controlled. Additionally, an acoustic or optical alarm signal also can indicate the receipt of an urgent e-mail. Icons for commands such as "new message", "read message", "transmission and/or reception report", "information" or "help" are reproduced in the e-mail window 18 in a known way, the actual message is displayed and other commands are also offered as word buttons.

Without leaving his workstation, the user, the radiologist and/or MRTA at one of the operator consoles 5 through 8 can read or input messages in an e-mail window on the picture screen for supporting the workflow.

The e-mail application can be a level 7 application according to the ISO-OSI layer model for communication protocols with particular attention to encryption and other security demands specifically of classes 1 and 2 for medical-technical devices. By displaying the e-mail on the console or backup console computer with connection to an RIS server 14, a system architecture is obtained with which, for example on a CT operator console 5, it is possible to receive an e-mail message in which the MTRA is notified of the emergency hospital admission of an accident victim for whom an whole-body CT scan should ensue immediately for fast overview diagnosis. The MRTA can then prepare the CT unit 1 for the procedure and keep it free instead of calling the next patient in the waiting room, so that the workflow of the emergency patient is not delayed. Additionally, requests and procedure can be electronically documented.

Further, for example, a fast diagnosis can be sent by e-mail directly from the modality to the requesting department, for example the intensive care station. For this, the RIS server 14 merely has to be provided with an e-mail client and the e-mail software merely has to be entered on the operator consoles 5 through 8 and viewing workstations 11 with arbitrary operating system and the necessary encryption software.

Although modifications and changes may be suggested by those skilled in the art, it is the intention of the inventor to embody within the patent warranted hereon all changes and modifications as reasonably and properly come within the scope of his contribution to the art.

I claim:

1. A medical system architecture comprising:
   a plurality of imaging modalities for respectively acquiring examination images, said modalities participating in a medical work flow and each of said imaging modalities having a modality console located at the imaging modality for operating the imaging modality;
   each of said modality consoles having a processor for processing the examination images respectively acquired by the modality having the modality console containing the processor, said processors also allowing data to be entered for association with said examination images;
   a transmission device connected to said processors for transmitting said data and said examination images from the modality having the modality console containing the processor;
   a memory connected to said transmission device for storing said data and examination images;
   a post-processor connected to said transmission system for post-processing said data and examination images;
   a server connected to said transmission system, said server being a client of an information system relating to said medical workflow; and
   a message system incorporated in said processors and said post-processor and connected to said server for making information relating to said medical workflow available at said processors, and thus available directly at the respective modality consoles, and said post-processor.

2. A medical system architecture as claimed in claim 1 wherein said server is an RIS server with an e-mail system as an RIS client.

3. A medical system architecture as claimed in claim 1 wherein said server is a workflow server having an e-mail system as a client.

4. A medical system architecture as claimed in claim 1 further comprising an e-mail server connected to said processors and said post-processor via said transmission system for exchanging e-mail messages.

5. A medical system architecture as claimed in claim 1 further comprising a plurality of monitors, respectively allocated to said processors and said post-processor, said processors and said post-processor causing a window to be displayed on the respective monitor allocated thereto, containing e-mail messages and related e-mail information associated with said medical workflow, in addition to displaying said examination images.

6. A medical system architecture as claimed in claim 5 wherein each of said processors and said post-processor marks respective e-mails dependent on the importance of the respective e-mails, with less important e-mails being displayed only with an indicator.

7. A medical system architecture as claimed in claim 6 wherein each of said processors and said post-processor has an acoustic signal generator which emits an acoustic signal upon receipt of a marked e-mail.

8. A medical system architecture as claimed in claim 6 wherein each of said processors and said post-processor has an optical signal generator which generates an optical signal on the monitor associated with the processor or post-processor upon receipt of a marked e-mail.

9. A medical system architecture as claimed in claim 1 wherein each of said processors and said post-processor encrypts said data.

10. A medical system architecture as claimed in claim 1 wherein each of said processors and said post-processor employs a level 7 application according to the ISO-OSI layer model for communication protocols.

11. A method for controlling workflow in a medical imaging and archiving system, comprising the steps of:
acquiring examination images respectively from a plurality of examining modalities, each having a modality console, said examining modalities participating in a medical workflow;
in a processor at each modality console, processing said examination images acquired by the examining modality connected thereto and, in each processor, entering data and associating the entered data respectively with said examination images;
connecting said processors to a transmission system;
connecting a memory to said transmission system for storing said data and images received, via said transmission system, from said processors;
connecting a post-processor to said transmission system and post-processing said data and said examination images therein, received from said processors and said memory via said transmission system;
connecting a server to said transmission system which is a client of an information system relating to said medical workflow; and
incorporating a message system in said processors and said post-processor for making information relating to said medical workflow available at said processors and thus available directly at the respective modality consoles and said post-processor.

12. A method as claimed in claim 11 comprising displaying said workflow information as an e-mail message respectively at said processors and said post-processor.

13. A method as claimed in claim 12 comprising marking important e-mails relating to said medical workflow and generating a humanly perceptible signal when a marked e-mail is received at one of said processors and said post-processor.

14. A method as claimed in claim 13 comprising identifying less important e-mails at said display with an indicator on said display.

15. A method as claimed in claim 11 comprising encrypting said data at said processors and said post-processor.

* * * * *